United States Patent
Zbikowski et al.

[11] Patent Number: 5,275,599
[45] Date of Patent: Jan. 4, 1994

[54] BIOCOMPRESSION EXTERNAL FIXATOR FOR OSTEOSYNTHESIS

[76] Inventors: Juan L. Zbikowski, Turia 20, 41011 Seville, Spain; Marcel H. Wagenknecht, Chemin des Milans 12, CH-1219 de Lignon, Switzerland

[21] Appl. No.: 993,484

[22] Filed: Dec. 18, 1992

Related U.S. Application Data

[63] Continuation of Ser. No. 883,795, May 14, 1992, which is a continuation of Ser. No. 773,751, Oct. 10, 1991, abandoned, which is a continuation of Ser. No. 631,762, Dec. 21, 1990, abandoned, which is a continuation of Ser. No. 506,486, Mar. 30, 1990, abandoned, which is a continuation of Ser. No. 283,010, Dec. 8, 1988, abandoned, which is a continuation of Ser. No. 84,269, Aug. 11, 1987, abandoned.

[30] Foreign Application Priority Data

Aug. 11, 1991 [ES] Spain ............................ 8603667

[51] Int. Cl.⁵ ........................................ A61B 17/18
[52] U.S. Cl. ............................................ 606/54; 606/53
[58] Field of Search .................. 384/51, 55; 606/53, 606/54, 55, 57, 58, 59, 86, 105

[56] References Cited

U.S. PATENT DOCUMENTS

| | | | |
|---|---|---|---|
| Re. 31,809 | 1/1985 | Danieletto et al. | 128/92 ZZ |
| 892,096 | 6/1908 | Taylor | 384/56 |
| 1,761,123 | 6/1930 | Gruver | 384/55 |
| 2,330,154 | 9/1943 | Stabinski | 384/55 |
| 2,391,537 | 12/1945 | Anderson | 128/92 Z |
| 2,520,453 | 8/1950 | Burmist | 384/55 |
| 2,970,016 | 1/1961 | Woldring | 384/55 |
| 3,003,830 | 10/1961 | Blazek et al. | 384/534 X |
| 3,054,648 | 9/1962 | Bauer | 384/51 |
| 3,210,135 | 10/1965 | Goller | 384/55 |
| 3,866,607 | 2/1975 | Forsythe et al. | 128/92 R |
| 4,096,857 | 6/1978 | Cramer et al. | 128/92 ZY X |
| 4,135,505 | 1/1979 | Day | 128/92 Z |
| 4,365,356 | 12/1982 | Broemer et al. | 128/92 YQ X |
| 4,450,834 | 5/1984 | Fischer | 128/92 UL |
| 4,475,546 | 10/1984 | Patton | 128/92 ZZ X |
| 4,488,542 | 12/1984 | Helland | 128/92 Z |
| 4,624,250 | 11/1986 | Saunders et al. | 128/92 VY |
| 4,628,922 | 12/1986 | Dewar | 128/92 Z |

FOREIGN PATENT DOCUMENTS

| | | | |
|---|---|---|---|
| 648808 | 9/1962 | Canada | 384/51 |
| 1346191 | 11/1963 | France | 384/51 |
| 2517535 | 11/1982 | France | 128/92 ZZ |
| 2001533 | 2/1979 | United Kingdom | 128/92 Z |

*Primary Examiner*—Robert A. Hafer
*Assistant Examiner*—Sam Rimell
*Attorney, Agent, or Firm*—Peter C. Richardson; Lawrence C. Akers; Raymond W. Augustin

[57] ABSTRACT

An external fixator includes two elements (20) of at least one pin (21, 22), each element maintaining a bone fragment (11; 12), and a telescopic piece (50 comprising an internal bar (41) and an external bar (42), each pin element being connected to either the internal or the external bar. One of the bars includes first guiding means for cooperation with corresponding second guiding means being at least indirectly dependent on the other bar, the first and second guiding means being separated from each other by roller sliding means intended to reduce the friction during the relative movement of the bars.

11 Claims, 5 Drawing Sheets

BIOCOMPRESSION EXTERNAL FIXATOR FOR OSTEOSYNTHESIS

This is a continuation, of application Ser. No. 07/883,795, filed on May 14, 1992, which is a continuation of application Ser. No. 07/773,751, filed Oct. 10, 1991, abandoned, which is a continuation of application Ser. No. 07/631,762, filed Dec. 21, 1990, abandoned, which is a continuation of application Ser. No. 07/506,486, filed Mar. 30, 1990, abandoned, which is a continuation of application Ser. No. 07,283,010, filed Dec. 8, 1988, abandoned, which is a continuation of application Ser. No. 07/084,269, filed Aug. 11, 1987, abandoned.

The present invention belongs to the field of esteosynthesis and more precisely concerns a biocompression external fixator.

External fixators have been known for many years and are used in bone surgery to maintain wires and transcutaneous pins inserted into the bones on each side of a fracture by means of external frames and fixation rods.

It has however been observed that in some cases, namely when using fixed systems giving nevertheless an excellent stability, there was a tendency toward delayed unions and scarce callus formation.

The so-called "biocompression" has been proposed in order to avoid such disadvantages. Biocompression is a term applied to the stresses (such as tractions and compressions) that have their origin in the deformation of a bone, under the loads of functional activities. The biocompression phenomena are also called, according to various authors: functional activity, mechanical stimuli, axial compression, load transmission or dynamization.

In fact, this biocompression has been stated to be an essential feature in the fracture healing which requires not only stability, which is not osteogenic in itself, but also physiologic biocompression. In fact, when a bone is loaded, it undergoes a deformation (strain) and at the same time, internal forces opposing this deformation (stresses) are built up. Elastic deformations occur when the original shape is recovered once the deforming load is removed. External fixators have been consequently considered both under rigidity and stability points of view, the term rigidity meaning the absence of elasticity and the term stability being the limitation to elastic deofrmations.

To perform such a biocompression, a device is needed allowing a sliding movement parallel to the bone axis in such a way that the muscular contraction is converted, at the fracture focus between the bone fragments, into a compression equal in magnitude and opposite to said contraction. The external fixator must cancel out any angular, lateral or rotational movement, while maintaining a sliding displacement in the direction of the longitudinal axis of the fractured bone. In the known systems, the compression is virtually invariable and its magnitude entirely empirical.

Many models of external fixators are already known, of various mechanical forms but essentially having the same principles: a plurality of transfixing pins or studs, inserted into each fragment of the fractured bone, are unified externally relative to the bone by means of metal frames or bars. The joining bars are of two types, namely neutralizing bars and compression bars.

The neutralizing bars are metal bars, generally made of steel, in several dimensions and shapes, which are connected to the bone pins by means of various clamping devices in order to constitute a fixed unit.

The compression bars are formed of fixable screw devices which make it possible to apply a permanent interfragmental compression being constant and substantially invariable. When the screw is fixed, the pressure applied is theoretically maintained constant within the period between two adjustments made by the physician. Alternatively, springs or rubber bands are used instead of screws.

A fixation system described in the Spanish Patent No. 483.191 is based on the utilization of telescopic sliding bars, formed by a double tube in which the exterior is greater in diameter and with an internal diameter corresponding to the outside of the interior tube. In order to fasten each one of the telescopic bars to one of the two fragments of a fractured bone, a bar is provided parallel to the principal axis of the bone to produce an axial compression in the area of the fracture under the muscular action. The fact that the muscle is never totally relaxed, even if the member is at rest, is therefore used since there exists a permanent contraction named muscular "tone". In other terms, the fracture is permanently submitted to various compressions being, from least to greatest importance:

muscular "tone" (when the member is at rest, including gravitational force),
muscular contractions due to movements,
static load (patient's weight)
dynamic loading when walking (depending on weight multiplied by acceleration),
all these stimulations being natural ones (hence the notion "biology" from the prefix "bio") and non mechanical such as those brought about by compression bars.

In order to avoid any angular displacement and any rotation at the site of the fracture, two telescopic bars are generally used, fixed on each extremity of the transfixing pins, i.e. pins extending from both sides of the member. As the sliding axis is to be disposed parallel to the longitudinal axis of the bone, these bars are maintained by means of clamping devices such as orientable jaws or ball-and-socket joints.

French Patent FR-82.19809 (U.S. Pat. No. 4,612,921) describes a functional attachment system for osteosynthesis by means of external fixators coupling the clamping devices of the transfixing studs inserted into the bone fragments, on each side of the fracture, by means of telescopically sliding bars acting as biocompressors. These bars are connected to the transfixing studs by means of jaws, ball-and-socket joints or other clamping devices, the compression mechanical stimuli at the focus, of physiological magnitude corresponding to the muscular tone and variable with the functional activity, the static load and the dynamic load being used as a functional attachment system.

That patent describes a system having several compression bars, in order to ensure the rotational stability. It is consequently disadvantageously cumbersome for the patient, since the fixation frame extends on each side of transfixing pins, i.e. on each side of the fractured member.

An object of the present invention is a device whose magnitude of compression varies as a function of parameters such as muscular tone (at rest), muscular contraction (from movements), the individual load (static) and the dynamic load (walk and weight by acceleration). This external fixator furthermore is advantageously the sole link between the groups of pins on each side of the fracture, which reduces the weight and the nuisance of the device for the patient.

Furthermore the device should be able to be very rapidly installed and adjusted, which is very important since the installation is made under anaesthesia, whose duration would consequently be significantly reduced.

The external fixator according to the invention comprises two groups of at least one pin, each maintaining a bone fragment, and a telescopic piece comprising an internal bar and an external bar, each group being connected to one of the internal and external bars. The device is characterized in that one of the bars includes first guiding means for cooperating with second guiding means interdependent at least indirectly with the other bar, said first and second guiding means being separated from each other by rolling sliding means intended to reduce the friction during the relative movement of the bars.

The said guiding means comprise at least one longitudinal flat surface made in one of the bars and capable of being arranged parallel to the longitudinal axis of the fractured bone.

The sliding means intended to reduce the friction can be realised in different ways, for example by means of a coating, for instance constituted by metallic microballs sunk in a coat of plastic. A needle bearing may also be used, for instance with a square section and constituted by a cage, each side of which is made of a separator presenting a succession of openings fitted to receive a needle each.

Alternatively the sliding means may be a ball bushing, fitted between two dirt scraper rings. This ball bushing is positioned between the movable bar and a guiding piece attached to the fixed bar.

In order to easily ensure the parallel alignment of the fractured bone with the telescopic piece, one of the bars would advantageously present an angulated end portion.

The accompanying drawings show, by way of example, two embodiments of the subject of the present invention. In the drawings.

Figure 1:
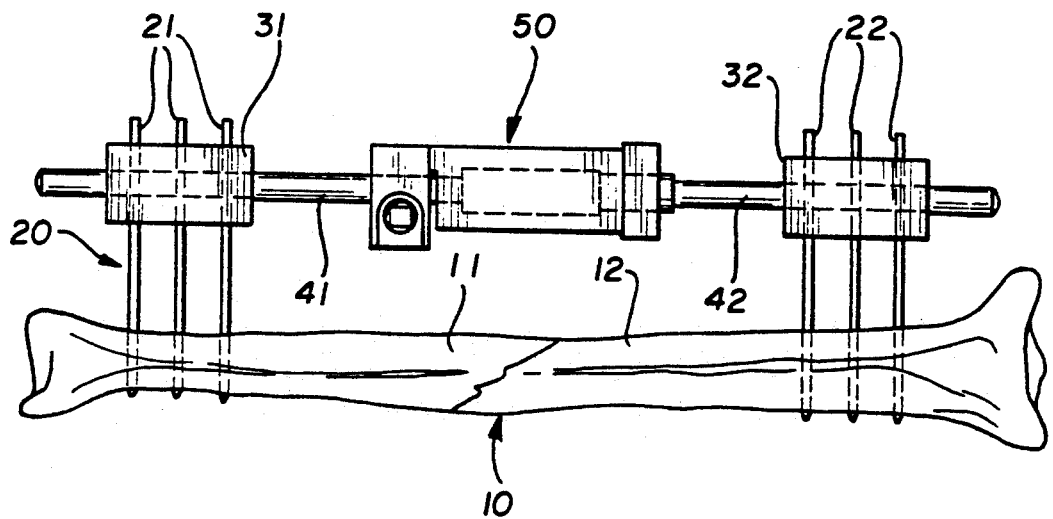
FIG. 1 is a general side elevation view schematically showing a fixator according to a first embodiment, as well as the anchoring means in the fractured bone.

In the schematical view represented in FIG. 1, a fractured bone 10 is represented in two parts 11 and 12. In each of the bone parts, one can distinguish a succession of studs or pins 20. More precisely there are in FIG. 1 a first group of three pins 21 inserted into the part 11 and a second group of pins 22 inserted into the bone part 12.

Each group of pins 21 or 22 is maintained in a corresponding binding piece 31 or 32, for instance a tightener, each jaw of which presents grooves for positioning and clamping the pins 21 and 22. The binding pieces 31 and 32 further connect the bars 41 and 42 foreseen to bind the two groups of pins 21 and 22, through the agency of a telescopic member 50. It is of course possible to replace the binding pieces 31 or 32 by orientable sockets according to any specific use.

Figure 2:
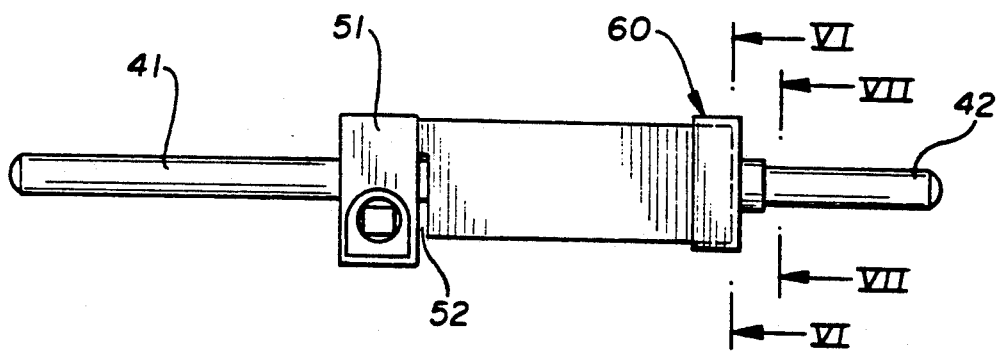
FIGS. 2 and 3 are partially enlarged views of the fixator shown in FIG. 1, respectively a side and a top view.
Figure 3:
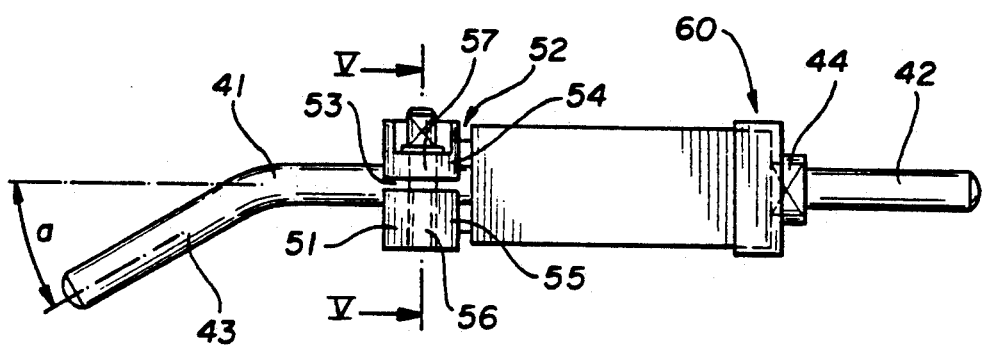

The FIGS. 2 and 3 present the enlarged telescopic member 50, with the precedingly described bars, the bar 41 being a fixed bar and the bar 42 a movable bar. The rear wall 51 of the member 50 is adapted to clamp the bar 41, whilst the front wall is closed by a tip 60, externally screwed on the member 50 and presenting an opening for the movable bar 42. It will be noted in FIG. 3 that the bar 41 presents an angulation $\alpha$, generally comprised between 20° to 90° beyond which the rear bar 43 is straight.

Figure 5:
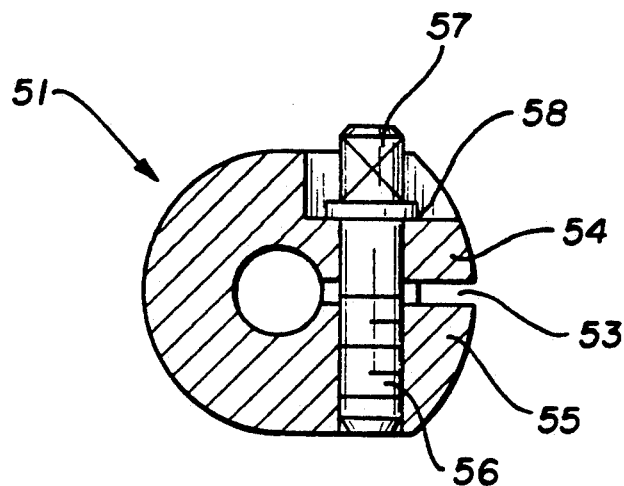
FIGS. 5, 6 and 7 are transversal section views taken respectively along the lines V—V, VI—VI and VII—VII in FIGS. 2 or 3 and respectively presenting the clamping device of one of the bars, the guiding means of the movable bar and the mounting tip.

The rear wall 51 presents a transversal slot 52 and a longitudinal slot 53 in order to create two wings 54 and 55, slightly deformable in order to allow the clamping of the bar 41. As visible in the sectional view of FIG. 5, the wing 55 presents a threaded opening 56 perpendicular to the slot 53 and adapted to receive a screw 57, freely crossing a corresponding opening in the wing 54, the screw head of which is leaning on the bottom of a therefor provided recess 58. It is to be noted that the screw 57 has a square head in order to cooperate with a corresponding securing wrench, and which is substantially on the same level as the member 50 when secured, hidden in the recess 58.

Figure 6:
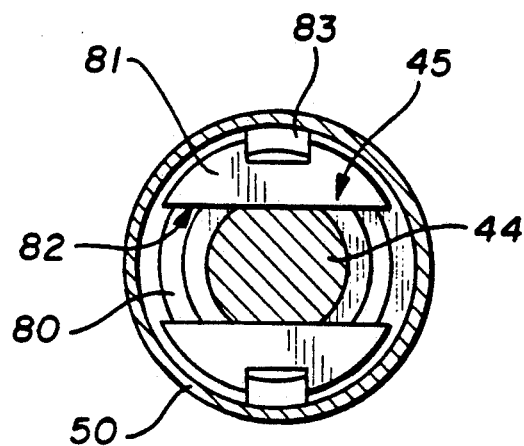
Figure 7:
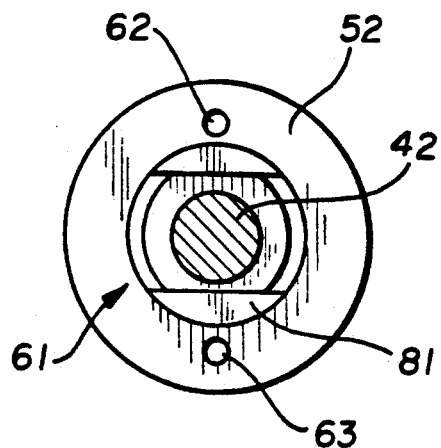

The bar 42 has a medium portion 44 of a diameter greater than that of the bar 42, with two longitudinal, parallel flat surfaces 45 as can be seen in FIG. 6 and able to guide the movable bar, in order to prevent its rotation.

Figure 4:
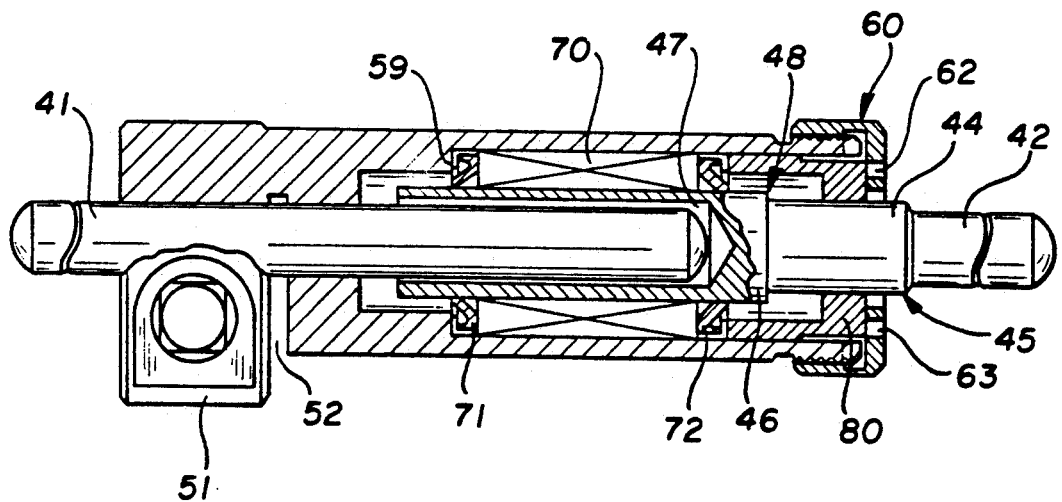
FIG. 4 is a longitudinal section view of the same device, further enlarged in order to show its principal parts.

Coming back to FIG. 4, it is to be noted that the rear portion 46 presents a central cylindrical opening 47, whose dimension is slightly greater than the diameter of the bar 41. The external diameter of the rear portion 46 is greater than the medium portion 44, in order to create an abutment 48.

Although the movable bar has been described in distinct portions 42, 44 and 46, in order to clarify the description, it is only one single part obtained by machining or eventually soldering the distinct parts.

The rear portion 46 of the movable bar is destined to cooperate with a ball bushing 70 in order to facilitate the relative sliding between both bars 41 and 42 and, more precisely, between the member 50, connected to the bar 41, and the bar 42. The ball bushing 70 is inserted in a corresponding central opening presenting an abutment 59 and is fixed between two dirt scraper rings 71 and 72.

The ball bushing furthermore cooperates with a guiding member 80 constituted by a cylindrical piece limited on one frontal face by a collar 81, whose diameter is superior to that of the cylindrical member 80. The collar 81 is adapted to abut on the member 50, while the cylindrical member 80 is engaged in the central opening of the member 50. The collar 81 presents a slot 82 whose width corresponds to the distance between the two longitudinal flat surfaces 45 of the medium portion 44 of the movable bar. The guiding member 80 is connected to the member 50 through two openings 83 adapted to cooperate with corresponding projections of the member 50.

The guiding member 80 is fixed in the member 50 by means of a tip 60, to be externally screwed on the member 50. The tip 60 has a circular opening 61 for the passage of the medium portion 44 of the movable bar. It furthermore presents two opposed holes 62 and 63 destined to receive two pins of a securing wrench in order to clamp the different parts mentioned above.

In order to limit the weight of the fixator, the member 50, its tip 60 and the guiding member 80 will be made from a light metal alloy, for instance from aluminum.

To ensure the rigidity of the device, the movable and fixed bars 41 and 42 will preferably be of stainless steel. It is to be noted that all these materials are resistant to sterilization conditions.

Figure 11:
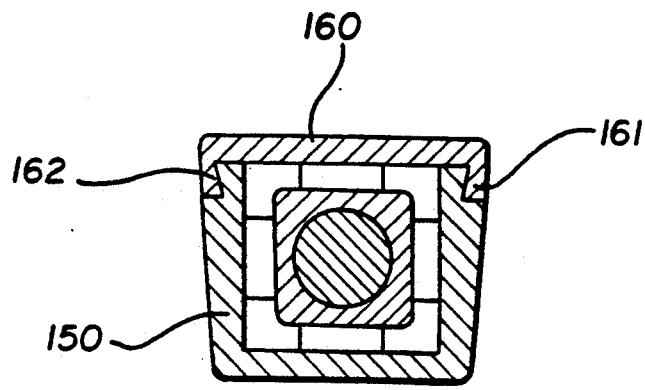
FIG. 11 is a transversal section view, taken along the line XI—XI in FIG. 10.

In the embodiment shown in FIGS. 8 to 11, there are a fixed bar 141 and a movable bar 142 having a medium portion 144 with a square section and whose dimension is greater than the diameter of the bar 142, in order to slide with respect to the member 150 and its top 160. This top presents two lateral lips 161 and 162 adapted to cooperate with two corresponding recesses in the member 150 (FIG. 11).

It will be noted that the medium portion 144 presents a graduated scale 145 in order to measure the relative movement. Although this scale was not mentioned in the first embodiment described, it may of course be fitted with that scale too.

The second embodiment essentially distinguishes in the fact that the medium portion 144 of the movable bar is of square cross-section. This portion is destined to slide in a needle bearing 170 constituted by a square prismatic casing, each side of which is made of a separator presenting a succession of rectangular openings 171 fitted to receive a needle 172 each. The medium portion 144 of the movable bar presents a central opening 147 adapted to receive the fixed bar 141 and its abuting plate 148.

Figure 9:
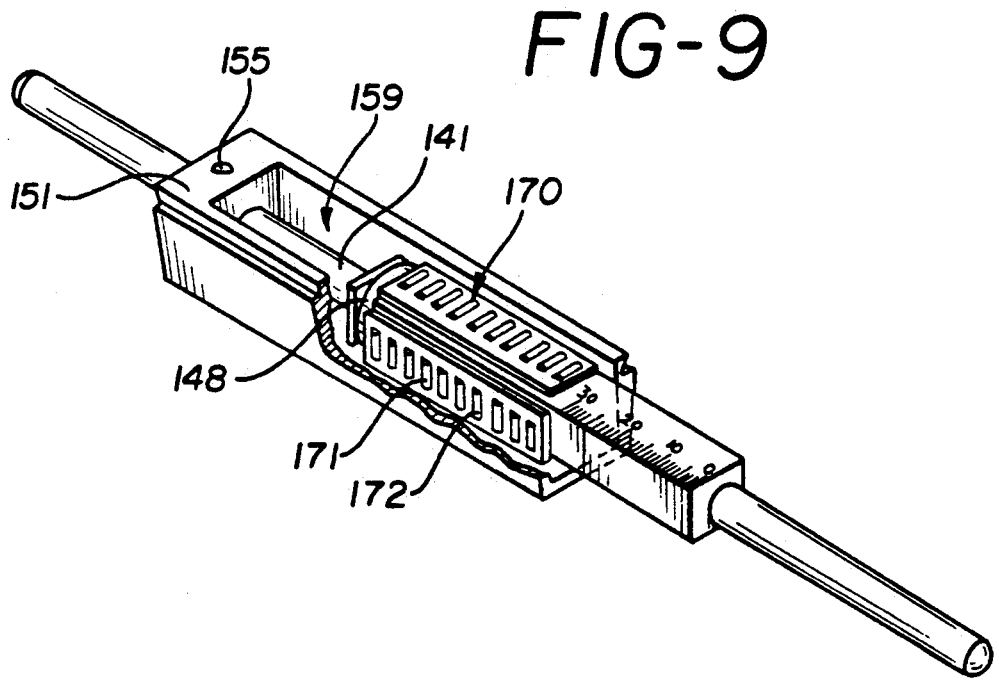
FIG. 9 is a partially sectional view of the device of FIG. 8, whose cover was removed.

The needle bearing 170 is disposed in a corresponding recess 159 in the member 150 as shown in FIG. 9, where the cover 160 is removed. It is to be noted that the member 150 is generally U-shaped, one end of which is closed by a fixed wall 151 and the other by a plate 180 having a square central opening 181 for the square bar 144. The cover 160 is adapted to slide along the member 150 and may be fixed within same by means of a screw 163 inserted into a corresponding recess 155 in the fixed wall 151. The fixed bar 141 is solidarised with the member 150 by means of a screw 157 cooperating with the tapping 156 therefor provided in the wall 151.

In the drawings the needle bearing 170 presents a square section. Without going beyond the scope of the present invention, the section may differ and be replaced by another polygonal shape, for instance triangular, quadrangular or hexagonal.

The fixed bar 141 and the movable ones 142 and 144 are generally made of stainless steel although other alloys are possible too, such as Cr-Co-Mo or titanium alloys, which have excellent mechanical properties and a relatively low weight.

The separators constituting the casing 170 may be realised in plastic materials such as high density polyethylene, nylon, teflon or others, under the conditions that the physical properties are appropriate and that they resist sterilization temperatures in saturated steam up to 140° C.

As already mentioned, the external fixator is to be installed during an operation under anaesthesia. Therefore it is particularly desirable to have available a mounted telescopic member in order to reduce the duration of the anaesthesia.

Figure 8:
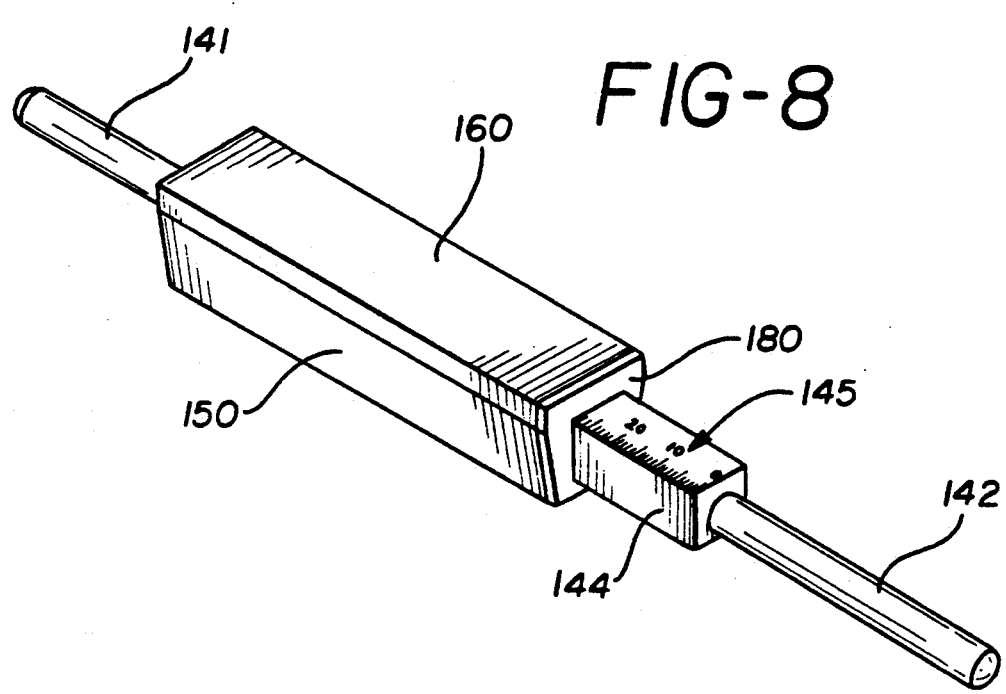
FIG. 8 is a perspective view of a second embodiment of the device according to the invention.
Figure 10:
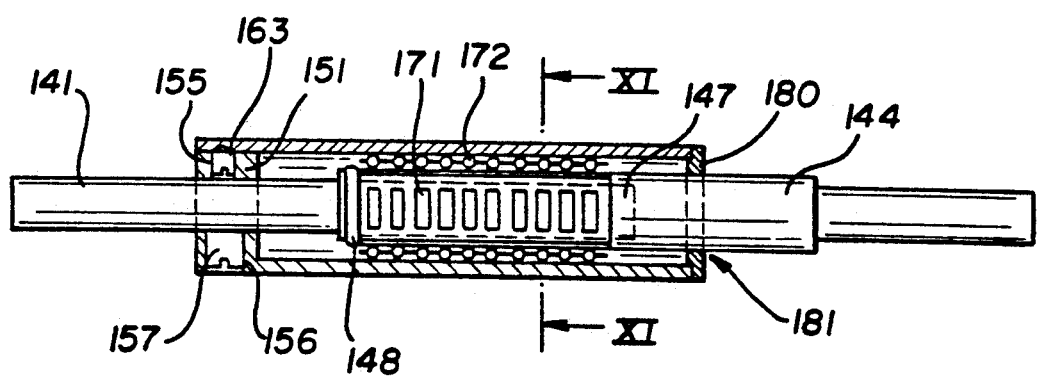
FIG. 10 is a longitudinal section view of the device of FIGS. 8 and 9, whilst

In the example of FIGS. 8 to 10, the square bar 144, surrounded by its needle bearing 170, is arranged in the recess 159 in the member 150. The lateral lips 161 and 162 of the cover 160 are slid along the corresponding recesses in the member 150, and the cover 160 is fixed within the member 150 by means of the screw 163 passed through the opening 156 for the clamping screw 157 and inserted into the corresponding tapping 155. The front plate 180 is fixed through any known means, and the fixed bar 141 is clamped by means of the screw 157.

In the embodiment shown in FIGS. 2 to 7, the ball bushing 70, surrounded by its two lateral scraper rings 71 and 72, is arranged around the rear portion 46 of the movable bar and engaged in the member 50 against the abutment 59 of the central opening. The guiding member 80 is placed around the medium portion 44 of the movable bar, in order to prevent any rotation of the movable bar 142 with respect to the member 50, as the longitudinal flat surfaces 145 are aligned in the corresponding slot 82. The tip 60 is mounted and fixed by means of a special securing tool having two pins destined to be introduced in the corresponding holes 62 and 63.

It is to be noted that, in any embodiment, the telescopic device, when mounted, is adapted to be subjected to sterilization treatments.

According to any particular use, the length and the shape of the fixed bar 41 will be chosen with respect to the bone for which the device is used and to the distance at which the pins are inserted in the bone fragments.

During the operation, the process of putting the device in place is the following: The physician first inserts the pins 21 and 22 into the bone fragments 11 and 12, on each side of the fracture. He then adjusts the telescopic member 50 or 150 parallel to the direction of the principal axis of the fractured bone 10, by means of the binding pieces 31 and 32.

To be sure that the compression displacement is parallel to the longitudinal axis of the fractured bone, the practitioner secures the fixed bar 41 or 141 within the rear wall 51 or 151 of the telescopic member 50 or 150, when turning the screw 57 or 157 in the corresponding tapping 56 or 156.

Coming back to FIG. 3 presenting a bar 41 with an angulated rear bar 43, one remarks that the alignment between the telescopic member and the fractured bone is easily obtained when rotating the telescopic member.

The compression movement is limited when the end of the fixed bar 41 abuts against the central opening 47 of the movable bar and the extension movement is limited by means of the abutment 48 in the guiding member 80.

We claim:

1. An external fixator for maintaining longitudinal axial alignment of bone fragments comprising:
 a first element comprising at least one pin and a second element comprising at least one pin, said at least one pin of said first element to be placed into a first bone fragment and said at least one pin of said second element to be placed in a second bone fragment;

a telescopic piece comprising, in a coaxial relationship with respect to a central longitudinal axis of said telescopic piece, an internal bar and an external bar, said first element being rigidly connected to and supported by said internal bar and said second element being rigidly connected to and supported by said external bar, said first and second elements extending at an angle to said central longitudinal axis of said telescopic piece so that a force generated by the loading of said first and second elements by axial compression of said bone fragments causes a bending moment to develop between said first and second bar, said external bar having a generally hollow interior for receiving said internal bar, the telescoping action of said internal bar within said external bar extending over a predetermined distance;

a roller sliding means disposed between said internal and external bars and extending in the longitudinal direction over at least said predetermined distance, said roller sliding means having a roller contact bearing having a multiplicity of rotatable elements spaced around the perimeter of engagement between said inner and external bars to provide support along all sides of the internal and external bars for spreading the forces generated by said bending moment over the entire length and perimeter of said roller sliding means; and guiding means disposed between said internal and external bars longitudinally spaced from said roller sliding means along said central longitudinal axis, said guiding means engaging at least one longitudinally extending flat surface formed on one of said bars, said flat surfaces extending in a plane parallel to the central longitudinal axis, said at least one longitudinally extending flat surface including a stop surface for engaging a stop surface connected to the other of said bars for limiting the relative longitudinal movement therebetween.

2. An external fixator according to claim 1, wherein external bar presents a central tubular opening whose dimension is greater than the diameter of the internal bar.

3. An external fixator according to claim 2, wherein said opening is cylindrical.

4. An external fixator according to claim 1, wherein at least one of said bars presents a graduated scale.

5. An external fixator according to claim 1, wherein said roller sliding means comprises a needle bearing.

6. An external fixator according to claim 5, wherein internal and external bars are square in cross section and said needle bearing presents a square cross section.

7. An external fixator according to claim 6, wherein said needle bearing comprises a prismatic casing, each side of which is made of a separator presenting a succession of openings fitted to receive a needle each.

8. An external fixator according to claim 7, wherein said needles are made of steel.

9. An external fixator according to claim 7, wherein said separators are made of plastics.

10. An external fixator according to claim 1, wherein said roller sliding means comprises a ball bushing.

11. An external fixator according to claim 10, wherein said ball bushing is fitted between two scraper rings.

* * * * *